United States Patent [19]
Scruggs

[11] Patent Number: 5,988,173
[45] Date of Patent: Nov. 23, 1999

[54] HEAD AND NECK IMMOBILIZATION SYSTEM

[76] Inventor: Sandy Scruggs, P.O. Box 1042, Mesilla, N.Mex. 88046

[21] Appl. No.: 09/078,056

[22] Filed: May 13, 1998

Related U.S. Application Data

[60] Provisional application No. 60/047,239, May 20, 1997.

[51] Int. Cl.⁶ ........................................................ A61F 5/37
[52] U.S. Cl. ............................................. 128/870; 5/637
[58] Field of Search .................................... 128/845, 846, 128/869, 870, 874, 875, 876; 5/630, 636, 637, 638, 640

[56] References Cited

U.S. PATENT DOCUMENTS

| | | | |
|---|---|---|---|
| 3,897,777 | 8/1975 | Morrison | 128/133 |
| 3,957,262 | 5/1976 | McReynolds | 5/637 |
| 4,297,994 | 11/1981 | Bashaw | 128/133 |
| 4,528,981 | 7/1985 | Behar | 128/133 |
| 4,655,206 | 4/1987 | Moody | 128/134 |
| 4,964,418 | 10/1990 | Wilson | 128/857 |
| 5,207,716 | 5/1993 | McReynolds et al. | 5/637 |
| 5,297,304 | 3/1994 | O'Sullivan | 5/630 |
| 5,382,226 | 1/1995 | Graham | 602/32 |
| 5,535,467 | 7/1996 | Ciske | 5/636 |

*Primary Examiner*—Michael A. Brown
*Attorney, Agent, or Firm*—Joseph N. Breaux

[57] ABSTRACT

A head and neck immobilization system includes a carrying bag; a rigid head, neck and shoulder support board having a curved forward pushing edge, two side mounted strap attachment slot members, a beveled leading edge, a T-shaped neck and shoulder support surface runway, and a U-shaped, hook and pile fastener covered, securing surface; a forehead securing assembly including a half-circular shaped forehead gripper, left and right elastic immobilizing straps, and metal securing clips secured to the ends of the immobilizing straps and securable to the strap attachment slot members of the support board; at least one gel filled posterior cervical spine support bag, the spine support bag including a gel filled spine support pouch, an adjustable volume support pouch adjustment reservoir, a lower hook and pile fastener material covered surface, and an upper hook and pile fastener material covered surface; and at least one elongated, cylindrical shaped around-the-helmet support, the around-the-helmet support being covered with hook and pile fastener material that is companionately securable to the hook and pile fastener material covering the U-shaped securing surface of the rigid support board.

1 Claim, 4 Drawing Sheets

HEAD AND NECK IMMOBILIZATION SYSTEM

This application claims benefit of provisional application 60/047,239 filed May 20, 1997.

TECHNICAL FIELD

The present invention relates to restraint systems and more particularly to a head and neck immobilization system for immobilizing the head, neck and shoulders of injured individuals that includes a carrying bag; a rigid head, neck and shoulder support board having a curved forward pushing edge, two side mounted strap attachment slot members, a beveled leading edge, a T-shaped neck and shoulder support surface runway, and a U-shaped, hook and pile fastener covered, securing surface; a forehead securing assembly including a half-circular shaped forehead gripper, left and right elastic immobilizing straps, and metal securing clips secured to the ends of the immobilizing straps and securable to the strap attachment slot members of the support board; at least one gel filled posterior cervical spine support bag, the spine support bag including a gel filled spine support pouch, an adjustable volume support pouch adjustment reservoir, a lower hook and pile fastener material covered surface, and an upper hook and pile fastener material covered surface; and at least one elongated, cylindrical shaped around-the-helmet support, the around-the-helmet support being covered with hook and pile fastener material that is companionately securable to the hook and pile fastener material covering the U-shaped securing surface of the rigid support board.

BACKGROUND OF INVENTION

Each year many athletes and other individuals are involved in accidents in which it is possible that head and neck injuries have resulted. Because it is impossible in some instances to detect and determine the extent of these head and neck injuries without advanced diagnostic tools such as X-rays and MRI scanning and in order to minimize further injury to persons suspected of having these types of injuries, it is standard procedure to immobilize the victim's head and neck during transportation of the victim to a diagnostic and treatment center. In many cases, improper or inadequate immobilization of the head and neck has resulted in serious injury to the victim that could possibly have been avoided by proper immobilization. It would be a benefit, therefore, to have a system for immobilizing the head and neck of an athlete or other individual suspected of sustaining a head and/or neck injury. Because these types of injuries can occur in remote locations, it would of course be a benefit to have such a system that included a carrying bag for conveniently carrying the elements of the immobilization system. Because the less movement of the head and neck regions of the individuals during the immobilization procedure the less injuries will be exacerbated during transport, it would be a benefit to have such an immobilization system that included a number of support pouches that could be positioned beneath regions of a person's neck and spine that could then be adjusted in size to fill the space between the neck and spine region of the accident victim and a rigid support board.

SUMMARY OF INVENTION

It is thus an object of the invention to provide a head and neck immobilization system.

It is a further object of the invention to provide a head and neck immobilization system that includes a carrying bag for conveniently carrying the elements of the immobilization system.

It is a still further object of the invention to provide a head and neck immobilization system that includes a number of support pouches that are positionable beneath regions of a person's neck and spine that are adjustable in size to fill the space between the spine region and a rigid support board of the immobilization system.

It is a still further object of the invention to provide a head and neck immobilization system that includes a carrying bag; a rigid head, neck and shoulder support board having a curved forward pushing edge, two side mounted strap attachment slot members, a beveled leading edge, a T-shaped neck and shoulder support surface runway, and a U-shaped, hook and pile fastener covered, securing surface; a forehead securing assembly including a half-circular shaped forehead gripper, left and right elastic immobilizing straps, and metal securing clips secured to the ends of the immobilizing straps and securable to the strap attachment slot members of the support board; at least one gel filled posterior cervical spine support bag, the spine support bag including a gel filled spine support pouch, an adjustable volume support pouch adjustment reservoir, a lower hook and pile fastener material covered surface, and an upper hook and pile fastener material covered surface; and at least one elongated, cylindrical shaped around-the-helmet support, the around-the-helmet support being covered with hook and pile fastener material that is companionately securable to the hook and pile fastener material covering the U-shaped securing surface of the rigid support board.

It is a still further object of the invention to provide a head and neck immobilization system that accomplishes all or some of the above objects in combination.

Accordingly, a head and neck immobilization system is provided. The head and neck immobilization system includes a carrying bag; a rigid head, neck and shoulder support board having a curved forward pushing edge, two side mounted strap attachment slot members, a beveled leading edge, a T-shaped neck and shoulder support surface runway, and a U-shaped, hook and pile fastener covered, securing surface; a forehead securing assembly including a half-circular shaped forehead gripper, left and right elastic immobilizing straps, and metal securing clips secured to the ends of the immobilizing straps and securable to the strap attachment slot members of the support board; at least one gel filled posterior cervical spine support bag, the spine support bag including a gel filled spine support pouch, an adjustable volume support pouch adjustment reservoir, a lower hook and pile fastener material covered surface, and an upper hook and pile fastener material covered surface; and at least one elongated, cylindrical shaped around-the-helmet support, the around-the-helmet support being covered with hook and pile fastener material that is companionately securable to the hook and pile fastener material covering the U-shaped securing surface of the rigid support board.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY EMBODIMENTS

Figure 1:
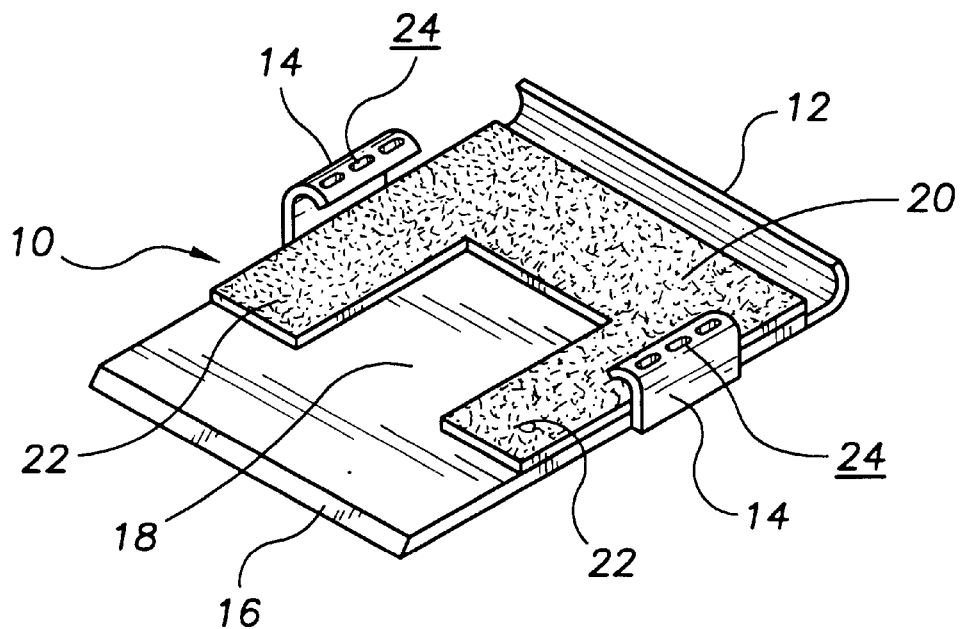
FIG. 1 is a perspective view of an exemplary embodiment of the rigid head, neck and shoulder support board of the head and neck immobilization system of the present invention showing the head, neck and shoulder support board member; the curved forward pushing edge of the support board; the side mounted strap attachment slot members; the beveled leading edge of the support board; the T-shaped neck and shoulder support surface runway of the support board; and the U-shaped hook and pile fastener covered securing surface of the support board.

FIG. 1 shows an exemplary embodiment of the rigid head, neck and shoulder support board of the head and neck immobilization system of the present invention, generally designated by the numeral 10. Support board 10 is approximately 16"×19" and is molded from rigid plastic. Support board 10 has a curved forward pushing edge 12; two side mounted strap attachment slot members 14; a beveled leading edge 16; a smooth surfaced, T-shaped neck and shoulder support surface runway 18; and a U-shaped hook and pile fastener covered securing surface 20. Curved forward pushing edge 12 provides a structure against which a first-aid provider can push to force support board 10 beneath the head, neck and shoulders of an injured person. To further assist this effort, support board 10 is provided with a beveled leading edge 16. In this embodiment, each of the strap attachment slot members 14 is integrally formed with support board 10 and includes a number of strap securing slots 24. In use, support board is inserted beneath the head, neck and shoulders of the person until the back of the head is positioned onto support surface runway 18 and located between two end sections 22 of securing surface 20.

Figure 2:
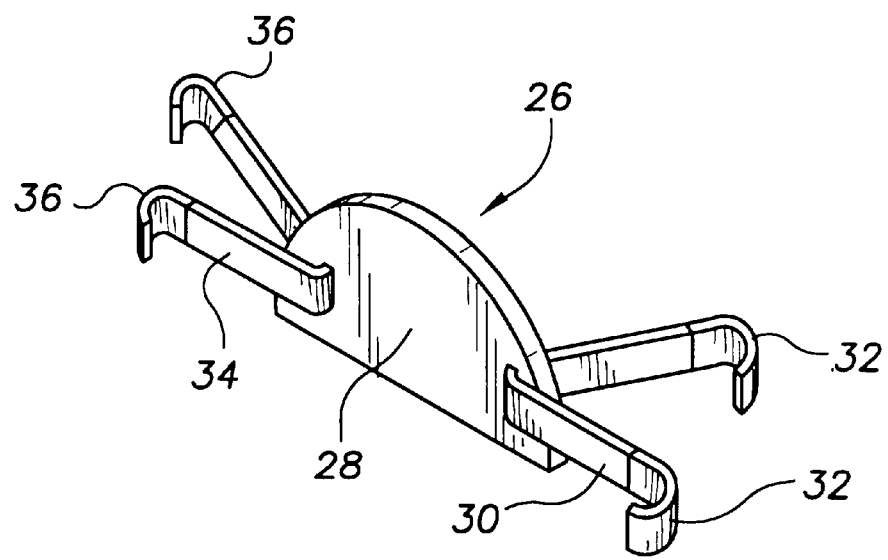
FIG. 2 is a perspective view of an exemplary embodiment of the forehead securing assembly of the head and neck immobilization system of the present invention showing the half-circular shaped forehead gripper, the left and right elastic immobilizing straps, and the metal securing clips.

FIG. 2 shows a forehead securing assembly of the head and neck immobilization system of the present invention, generally indicated by the number 26. Forehead securing assembly 26 includes a half-circular shaped, flexible plastic forehead gripper 28, a left elastic immobilizing strap 30 including two metal securing clips 32, and a right elastic immobilizing strap 34 including two metal securing clips 36. Forehead securing assembly 26 is used in conjunction with support board 10 to secure the forehead of a person by attaching securing clips 32, 36 to strap attachment slot members 14 using strap securing slots 24.

Figure 3:
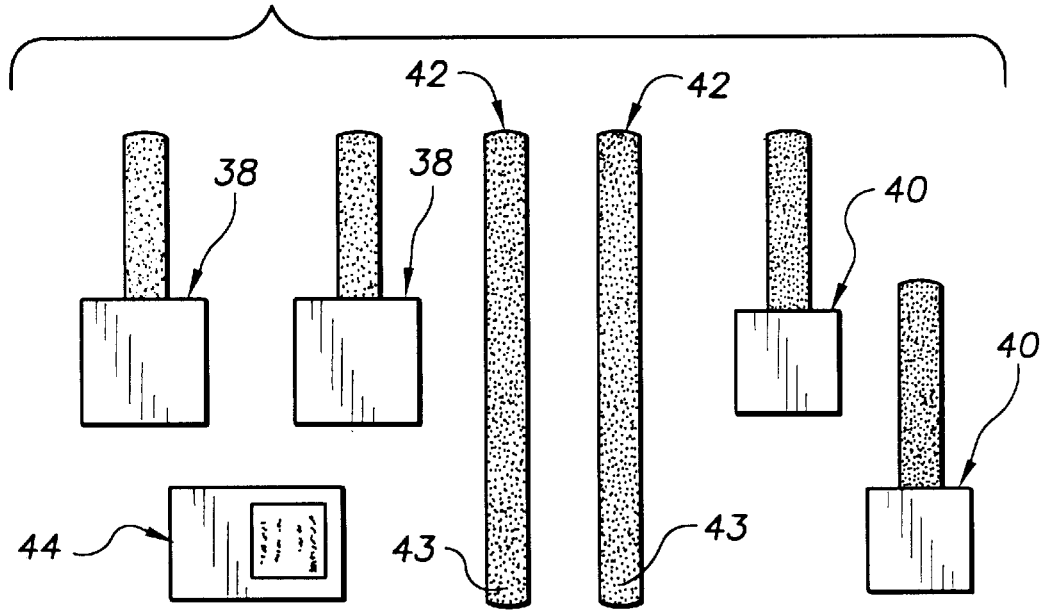
FIG. 3 is a top plan view of exemplary embodiments of the mallet shaped, gel filled posterior cervical spine support bags; the elongated, cylindrical shaped, foam bead filled around-the-helmet supports; and an adhesive backed injury report form with pee off backing of the head and neck immobilization system of the present invention.

FIG. 3 shows two exemplary large sized cervical spine support bags, generally designated 38; two exemplary medium sized cervical spin support bags, generally designated 40; two exemplary elongated around-the-helmet supports, generally designated 42; and an exemplary adhesive backed injury report form 44 with peel of backing sheet of the head and neck immobilization system of the present invention. Each of the around-the-helmet supports is an elongated flexible plastic tube filled with BB sized foam beads. The exterior surface 43 of each around-the-helmet support 42 is covered with hook and pile fastener material that adheres to and bonds with the U-shaped hook and pile fastener covered securing surface 20 of support board 10 (FIG. 1). In use, around-the-helmet supports 42 are positioned onto securing surface 20 of support board 10 to define a confined area surrounding the head or helmet of an injured person or athlete.

Figure 3A:
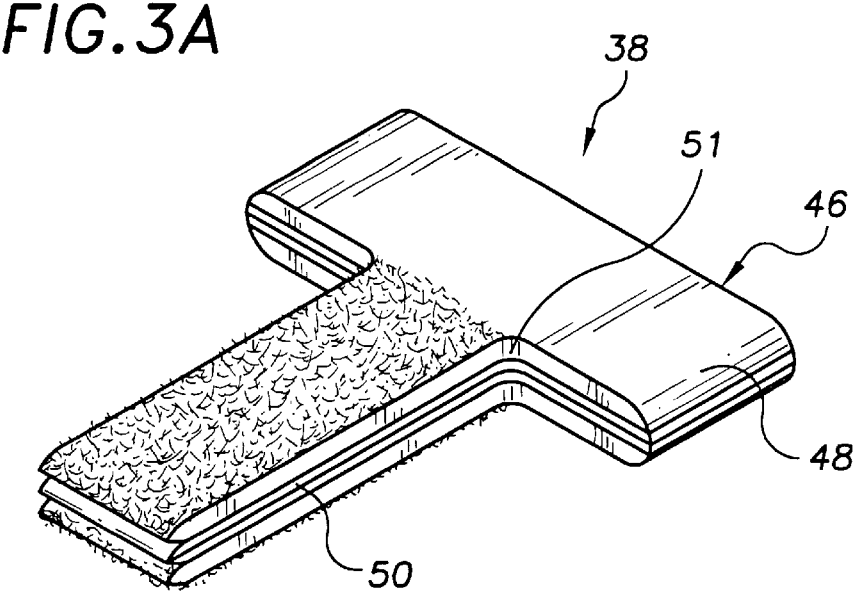
FIG. 3A is a perspective view of one of the exemplary mallet shaped gel filled posterior cervical spine support bags of FIG. 3 showing the gel filled spine support pouch, the adjustable volume support pouch adjustment reservoir, the lower hook and pile fastener material covered surface, and the upper hook and pile fastener material covered surface.

Large support bags 38 and medium support bags 40 are identical in construction and differ only in dimensions. While the following discussion is directed to a support bag 38, the discussion is intended to be equally applicable to all support bags 38, 40. Referring now to FIG. 3A, cervical spine support bag 38 is substantially mallet shaped and includes a gel filled, mallet shaped bag, generally designated 46, of sonically welded plastic sheeting construction. Bag 46 includes a gel filled spine support pouch 48 and an elongated, adjustable volume support pouch adjustment reservoir 50 that extends from the center sidewall 51 of spine support pouch 48. Support pouch 48 and pouch adjustment reservoir 50 are in gel flow connection in a manner such that gel within either can be shifted from one to the other.

Figure 3B:
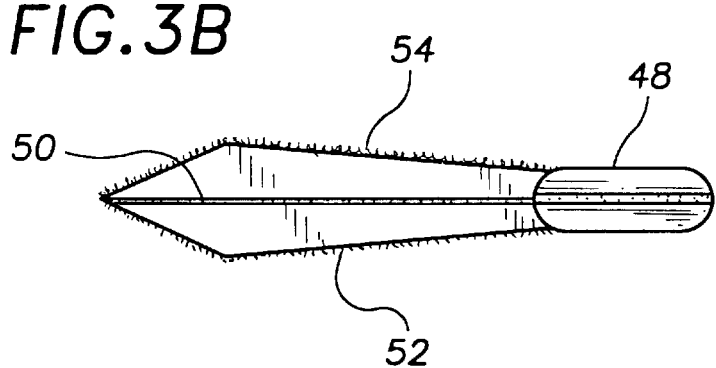
FIG. 3B is a side plan view of the exemplary gel filled posterior cervical spine support bag of FIG. 3A showing the gel filled spine support pouch in its fully compressed state and the adjustable volume support pouch adjustment reservoir fully unrolled in the fully filled state.
Figure 3C:
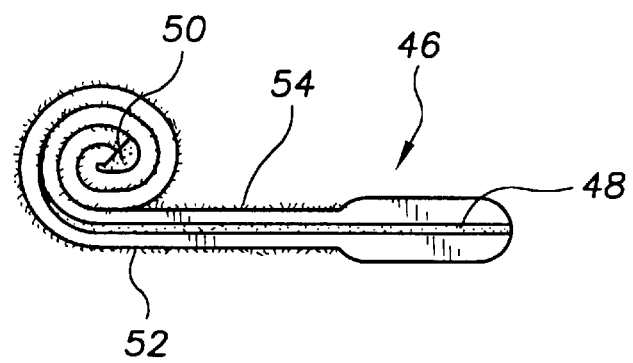
FIG. 3C is a side plan view of the exemplary gel filled posterior cervical spine support bag of FIG. 3A showing the gel filled spine support pouch in its partially filled state and the adjustable volume support pouch adjustment reservoir partially rolled.

With reference to FIG. 3B, the lower surface 52 of pouch adjustment reservoir 50 is covered with hook and pile fastener material of a first type. The upper surface 54 of pouch adjustment reservoir 50 is covered with hook and pile fastener material of a second type. When hook and pile material of the first and second type contact each other a bond is formed. In use, a first-aid provided can adjust the size of spine support pouch 48 by, with reference now to FIG. 3C, rolling pouch adjustment reservoir 50 into a roll in a manner such that lower surface 52 contacts and bonds with upper surface 54. As adjustment reservoir 50 is rolled, gel within adjustment reservoir 50 is forced into spine support pouch 48 causing it to increase in size. Once spine support pouch 48 has achieved the desired size, rolling of adjustment reservoir 50 is halted. The bond between lower surface 52 and upper surface 54 prevents adjustment reservoir from unrolling and maintains spine support pouch 48 at the desired size.

Figure 4:
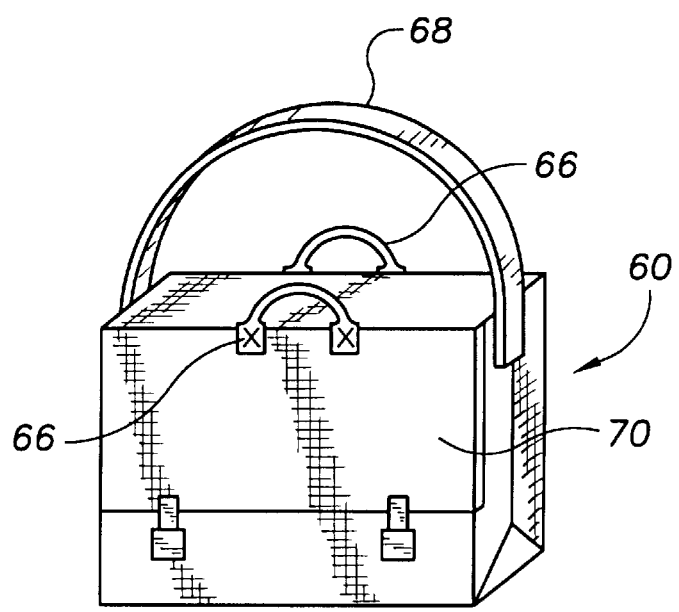
FIG. 4 is a perspective view of the exemplary carrying bag of the head and neck immobilization system of the present invention showing the carrying handles, the over-the-shoulder carrying strap, and the clip-shut flap.
Figure 5:
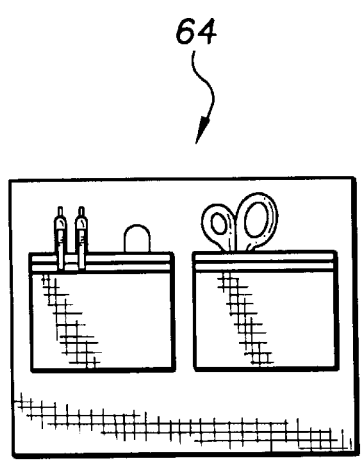
FIG. 5 is a plan view of the organizer sleeve positioned beneath the clip-shut flap of the exemplary carrying bag of FIG. 4.

FIG. 4 shows an exemplary carrying bag, generally designated 60, that is provided for carrying and storing support board 10 (FIG. 1), forehead securing assembly 26 (FIG. 2), large sized cervical spine support bags 38, medium sized cervical spin support bags 40, elongated around-the-helmet supports 42, and adhesive backed injury report forms 44 (all of FIG. 3) of the head and neck immobilization system of the present invention as well as an organizer sleeve 64 (shown in FIG. 5). Carrying bag 60 is of conventional fabric construction and includes a pair of carrying handles 66, an over-the-shoulder carrying strap 68, and a clip-shut flap 70. With reference now to FIG. 5, clip-shut flap 70 covers a removable organizer sleeve 64. In this embodiment, organizer sleeve 64 includes a number of items such as a number of pens, a penlight, a pocket knife, a pair of scissors, a face guard, a supply of gauze padding, several pairs of latex gloves, and various other first-aid items that can be used to assist in immobilizing the neck, head and shoulders of a person as well as provide needed information regarding the nature and facts surrounding the potential injury.

Figure 6:
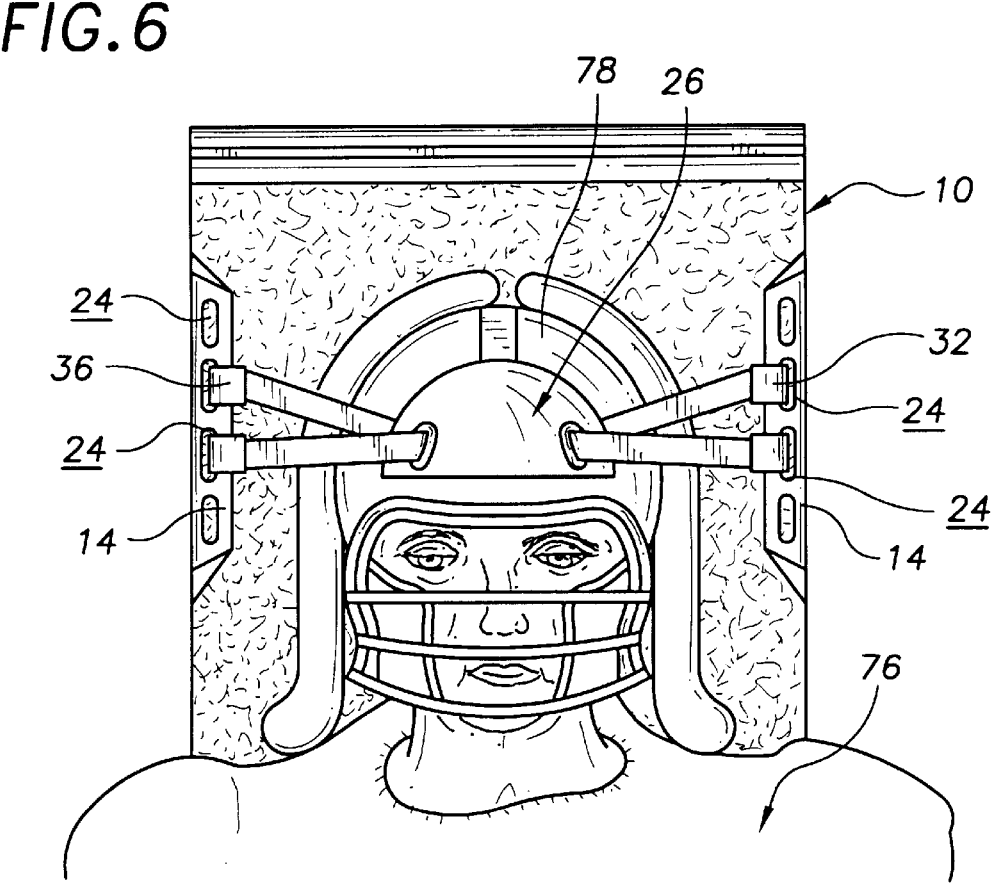
FIG. 6 is a top plan view of a representative football player with his head and neck immobilized using elements of the exemplary head and neck immobilization system of the present invention.

With reference now to FIG. 6, the head and neck mobilization system of the present invention is used, for instance, to immobilize the head and neck of athletes who may have sustained potential head and neck injuries. The system is used by inserting support board 10 gently beneath the neck, head and shoulders of an athlete 76 as previously discussed herein before. In this exemplary application, the helmet 78 is not removed as in many instances it is often unwise to remove the helmet 78 prior to immobilizing the head and neck. Once the head and neck are correctly positioned onto support board 10, forehead securing assembly 26 is used in conjunction with support board 10 to secure the forehead of a person by attaching securing clips 32, 36 to strap attachment slot members 14 using strap securing slots 24. Around-the-helmet supports 42 are then positioned onto securing surface 20 of support board 10 to define a confined area surrounding helmet 78. The first aid provider then selects the desired size of cervical spine support bag 38, 40 and places the spine support pouch 48 under the area to be supported. The size of spine support pouch 48 is then easily adjusted by rolling pouch adjustment reservoir 50 into a roll as previously described. Relevant information is then recorded on the adhesive backed injury report form 44, the peel off backing removed, the adhesive backed injury report form adhesively secured to the clothing of the injured party in a conspicuous location. The individual is then ready for transport to a medical facility.

It can be seen from the preceding description that a head and neck immobilization system has been provided that includes a carrying bag for conveniently carrying the elements of the immobilization system; that includes a number of support pouches that are positionable beneath regions of a person's neck and spine that are adjustable in size to fill the space between the spine region and a rigid support board of the immobilization system; and that includes a carrying bag; a rigid head, neck and shoulder support board having a curved forward pushing edge, two side mounted strap attachment slot members, a beveled leading edge, a T-shaped neck and shoulder support surface runway, and a U-shaped, hook and pile fastener covered, securing surface; a forehead securing assembly including a half-circular shaped forehead gripper, left and right elastic immobilizing straps, and metal securing clips secured to the ends of the immobilizing straps and securable to the strap attachment slot members of the support board; at least one gel filled posterior cervical spine support bag, the spine support bag including a gel filled spine support pouch, an adjustable volume support pouch adjustment reservoir, a lower hook and pile fastener material covered surface, and an upper hook and pile fastener material covered surface; and at least one elongated, cylindrical shaped around-the-helmet support, the around-the-helmet support being covered with hook and pile fastener material that is companionately securable to the hook and pile fastener material covering the U-shaped securing surface of the rigid support board.

It is noted that the embodiment of the head and neck immobilization system described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be Interpreted as illustrative and not in a limiting sense.

What is claimed is:

1. A head and neck immobilization system comprising:

a carrying bag;

a rigid head, neck and shoulder support board having a curved forward pushing edge, two side mounted strap attachment slot members, a beveled leading edge, a T-shaped neck and shoulder support surface runway, and a U-shaped, hook and pile fastener covered, securing surface;

a forehead securing assembly including a half-circular shaped forehead gripper, left and right elastic immobilizing straps, and metal securing clips secured to ends of said immobilizing straps and securable to said strap attachment slot members of said support board;

at least one gel filled posterior cervical spine support bag, said spine support bag including a gel filled spine support pouch, an adjustable volume support pouch adjustment reservoir, a lower hook and pile fastener material covered surface, and an upper hook and pile fastener material covered surface; and at least one elongated, cylindrical shaped around-the-helmet support, said around-the-helmet support being covered with hook and pile fastener material that is companionately securable to said hook and pile fastener material covering said U-shaped securing surface of said rigid support board.

* * * * *